United States Patent [19]

Doughty

[11] 4,223,862
[45] Sep. 23, 1980

[54] PATIENT SUPPORT APPARATUS

[76] Inventor: Val J. Doughty, P.O. Box 26075, Tempe, Ariz. 85282

[21] Appl. No.: 961,984

[22] Filed: Nov. 20, 1978

[51] Int. Cl.³ ............................................. A47B 96/06
[52] U.S. Cl. ............................... 248/222.3; 211/105.1; 403/263
[58] Field of Search ............... 248/222.3, 222.2, 222.4, 248/223.1, 223.2, 223.4, 224.1, 224.2, 224.4, 221.3, 118.1; 211/103, 105.1; 250/491; 403/263, 187

[56] References Cited

U.S. PATENT DOCUMENTS

| 633,987 | 10/1899 | Clough | 211/103 X |
|---|---|---|---|
| 2,151,224 | 3/1939 | Neely | 250/491 |
| 2,336,604 | 12/1943 | Edward et al. | 211/103 X |
| 2,458,897 | 1/1949 | De Swart | 248/222.3 |
| 2,573,348 | 10/1951 | Meadows | 211/103 |
| 2,608,843 | 9/1952 | Kennedy | 248/222.3 |
| 2,626,711 | 1/1953 | Saul et al. | 248/221.3 X |
| 2,707,564 | 5/1955 | Smith | 211/103 X |
| 3,045,962 | 7/1962 | Paulus | 248/222.3 |
| 3,080,980 | 3/1963 | Gibbons | 248/222.3 |
| 3,087,625 | 4/1963 | Coon | 211/103 |
| 3,129,751 | 4/1964 | Weber | 248/222.3 X |
| 3,588,020 | 6/1971 | Newcomer | 248/222.3 |

FOREIGN PATENT DOCUMENTS 463250 7/1928 Fed. Rep. of Germany ........... 250/491
479518 7/1929 Fed. Rep. of Germany ........... 250/491

Primary Examiner—J. Franklin Foss
Attorney, Agent, or Firm—LaValle D. Ptak

[57] ABSTRACT

A patient support apparatus for use with medical X-ray equipment to provide a convenient arm support for patients during the time medical X-rays are being taken comprises an elongated rectangular anchor member mounted on the wall adjacent the medical X-ray apparatus. The anchor member has a number of vertically aligned apertures formed in it for receiving a horizontally extending arm support bar. The support bar is dimensioned to fit snugly into the various apertures and can be removed readily from any one of such apertures for re-insertion into another aperture. This permits adjustment of the height of the support bar relative to the X-ray equipment to accommodate patients of different heights and to adapt the support bar for use with standing patients or patients who are sitting on an examination table adjacent the X-ray apparatus.

9 Claims, 6 Drawing Figures

U.S. Patent  Sep. 23, 1980  4,223,862

PATIENT SUPPORT APPARATUS

BACKGROUND OF THE INVENTION

Medical X-ray units of the type typically used in hospitals and emergency rooms generally employ a radiographic stand mounted on the wall or mounted on a vertical support post in the center of the room in which the X-ray unit is used. Such stands are used for many applications, such as to obtain X-rays of the chest, abdomen, pelvis, skull and spinal column of patients. Various accessories are used to adapt the X-ray unit to these various applications, such as the provision of head supports for skull X-rays.

When a conventional wall mounted X-ray unit is utilized for obtaining radiographs of the chest, it is necessary for the patient to hold his or her arms up out of the way of the chest region of the body. This is true whether the patient is standing or whether the patient is sitting on an examination table adjacent the X-ray unit. In many cases, patients who are having such radiographs made of their chest region are in a weakened or feeble condition. This is particularly true of older patients who find it very difficult to hold their arms up for the length of time required to make the necessary radiographs.

In an effort to assist patients, particularly elderly patients, during the taking of chest radiographs, it has been the practice in the past for some X-ray technicians to hold onto the arms of the patient while the radiograph is being made. Although the patient receives the required steadying support from this action, the X-ray technician risks himself to unnecessary and dangerous exposure to radiation. In many hospitals and X-ray laboratories, the support for a patient to use to hold his or her arms up out of the way during a chest X-ray is provided by any available apparatus in the room having a sufficient height. Often this apparatus is an I-V stand used for holding the various solutions in intravenous feeding. Such stands are not designed as arm supports and consequently are very unstable when they are used in this manner. It is easy to tip over such a stand when it is used as a patient arm support, thereby risking the danger of a fall to a patient who is already in a feeble physical condition.

At least one manufacturer of X-ray equipment has added a patient holder to the wall stand of the X-ray unit. The holder extends out of the top of the wall stand and laterally over the area where the patient stands in front of the radiographic plate. A swivel T-bar is attached to the end of the patient holder arm, so that the patient can grasp the bar over his or her head and hold onto it during the time a chest X-ray is being taken. Such a bar, however, necessarily has a very limited vertical height adjustment and has not been found to provide the assurance of stability to a patient using the bar.

Accordingly, it is desirable to provide a patient support for use in conjunction with X-ray units which is simple in construction, reliable, and which provides a stable support for the arms of a patient during the operation of the X-ray unit. It also is desirable for such a support to be capable of different heights and to permit use of the support for patients standing in front of the X-ray machine as well as for patients who are seated on a bed or examination table.

SUMMARY OF THE INVENTION

Accordingly, it is an object of this invention to provide an improved patient support.

It is another object of this invention to provide an improved patient arm support for use in conjunction with X-ray units.

It is an additional object of this invention to provide an improved patient support which is simple and effective to provide stable support for the arms of a patient during the taking of radiographs by an X-ray unit.

It is a further object of this invention to provide an improved patient arm support for use in conjunction with X-ray units which is capable of simple and rapid vertical adjustment to accommodate patients of different sizes.

It is still another object of this invention to provide a wall-mounted patient arm support for use in conjunction with X-ray apparatus.

In accordance with a preferred embodiment of this invention, a patient support apparatus includes an anchor member of a predetermined thickness and having a number of apertures located at different positions in it for receiving a support bar. The anchor member is mounted on a wall and the dimensions of the support bar are selected to cause it to snugly fit into the apertures to extend outwardly from the anchor member. The support bar is made to removably fit into the apertures; and in a more specific embodiment of the invention, a mating key-way in the apertures and key-way engaging tabs on the support bar are used to secure the support bar in a selected aperture to prevent its accidental dislodgement.

DETAILED DESCRIPTION

Figure 1:
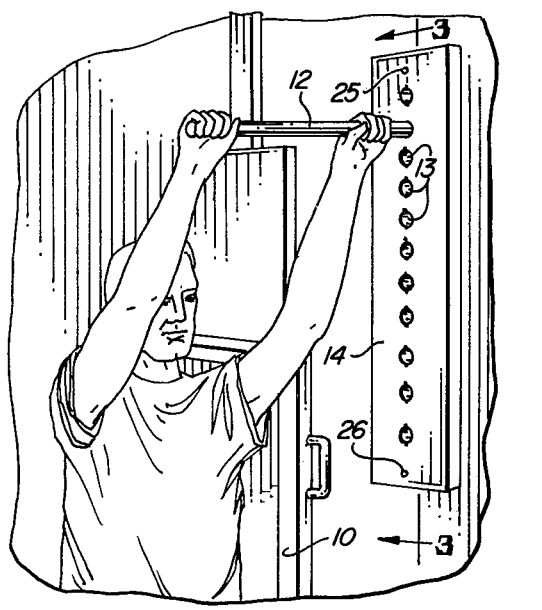
FIG. 1 shows the use of a preferred embodiment of the invention in conjunction with a wall mounted X-ray apparatus.

Reference now should be made to the drawing in which the same reference numbers are used throughout the different figures to designate the same or similar components. FIG. 1 shows a patient standing alongside a wall mounted radiographic unit 10 of a conventional X-ray apparatus. The unit 10 is vertically adjustable along a vertical positioning bar in a conventional manner to adjust for patients of different heights, or to make a suitable adjustment between patients who are standing on the floor next to the X-ray unit or who are sitting on an examination table next to the unit.

To assist an X-ray technician in the taking of chest X-rays, a support bar 12 is inserted into an appropriate one of a number of vertically aligned apertures 13 in a wall mounted anchor member 14. The anchor member 14 is mounted on the wall to the right of the vertical path of travel of the unit 10 of the X-ray apparatus; so that a person standing or seated adjacent the unit 10 may grasp the bar 12, as illustrated in FIG. 1, to steady himself and lift his arms up out of the way while the chest X-ray is being taken.

Since approximately 95 percent of all side chest X-rays are taken with the left side of the patient against the radiograph unit it generally is sufficient to employ only a single anchor member 14, located as shown in FIG. 1. For situations, however, where an X-ray is desired with the right side of the patient against the unit 10, a second wall mounted anchor plate 14 may be located on the opposite side of the vertical path of travel of the radiographic unit 10 if desired. The location shown in FIG. 1, however, is adequate for most side chest X-rays.

The depth of the anchor member 14 in the region of the apertures or holes 13 is selected to provide a firm support for the holding bar 12 when a downward force is subjected to the holding bar 12 by the patient grasping the bar. The outer diameter of the holding bar 12 is selected to snugly fit into the apertures 13, so that a firm and secure "feel" is given to the patient grasping the bar during the time the X-ray is being taken.

Different apertures 13 vertically aligned in the anchor member 14 are used to permit vertical adjustment of the holding bar 12 to accommodate for variations in patients' height and to accommodate for variations which are encountered between standing patients and patients seated on an examining table. An adequate vertical range of adjustment between the bottom aperture 13 and the top aperture 13 has been found to be on the order of thirty-six inches. This range is found to be sufficient to accommodate height differences in patients ranging from a small child to a tall adult.

Figure 2:
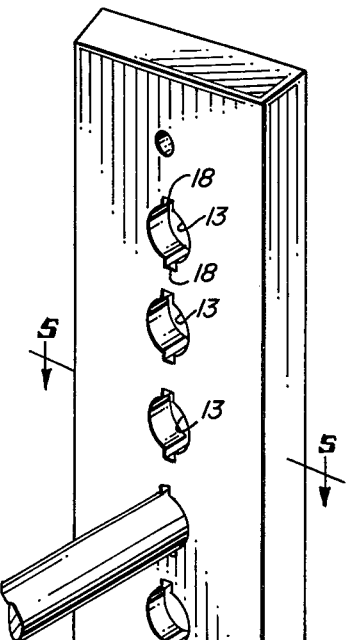
FIG. 2 is a partially cut away perspective view of a preferred embodiment of the invention.

To facilitate rapid and easy relocation of the support bar 12 from one aperture 13 to another, the external diameter of the support bar 12 is made to be slightly less than the internal diameter of each of the apertures 13. On opposite sides of each of the apertures 13 are a pair of key-way slots 18. These are shown most clearly in FIG. 2, and are located on the upper and lower sides of the apertures 13. These key-way slots 18 are made to accommodate a pair of tabs 15 and 16 located near the end of the support rod 12 when the support rod 12 is inserted into an appropriate one of the apertures 13.

Figure 3:
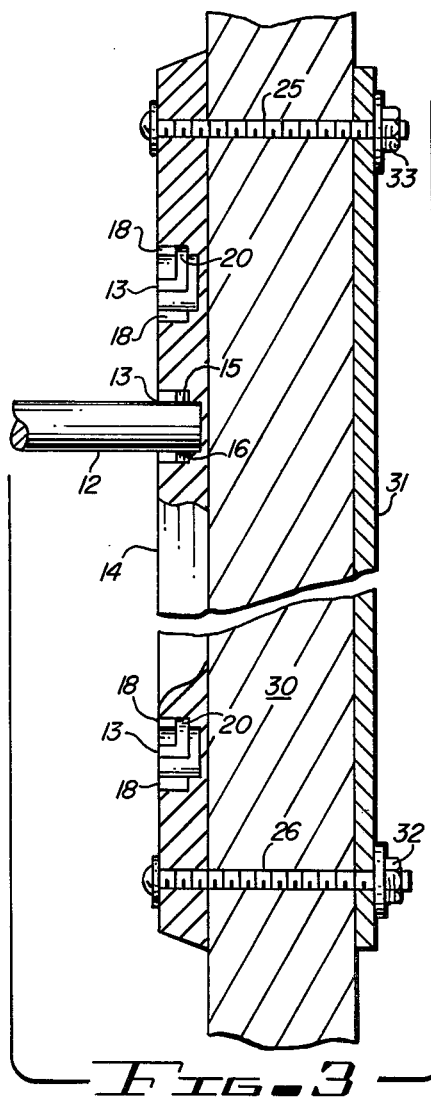
FIG. 3 is a partial longitudinal cross-sectional view of the embodiment shown in FIG. 2.

The depth to which the support rod 12 may be inserted is established by the depth of the apertures 13 in the anchor member 14, as indicated most clearly in the cross-sectional view shown in FIG. 3. The bottom of each of these apertures 13, which do not extend all the way through the anchor member 14 establishes a shoulder against which the end of the support bar 12 rests when the support bar is inserted fully into any one of the apertures 13. After the support bar 12 is fully inserted, it then is turned 90 degrees in a counter-clockwise direction (as viewed in FIG. 4) to cause the extending tabs 15 and 16 to enter a respective pair of semicircular key-way slots 20 which undercut the main body portion of the anchor member 14, as illustrated most clearly in FIG. 4. This prevents accidental dislodgement of the support bar 12 when it is in place for use by a patient in the manner illustrated in FIG. 1.

Figure 4:
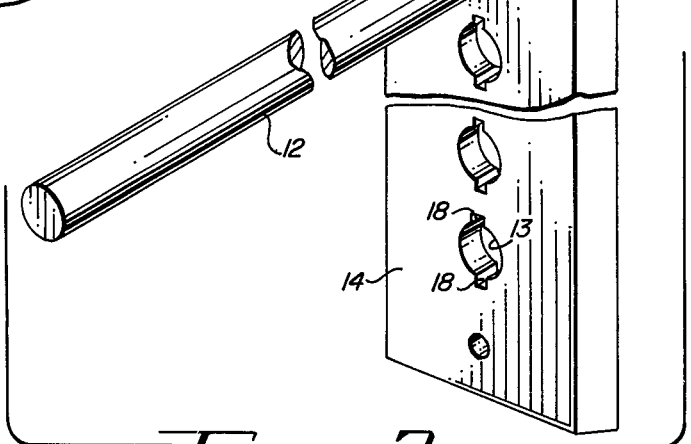
FIG. 4 shows details of a portion of the embodiment shown in FIG. 2.
Figure 5:
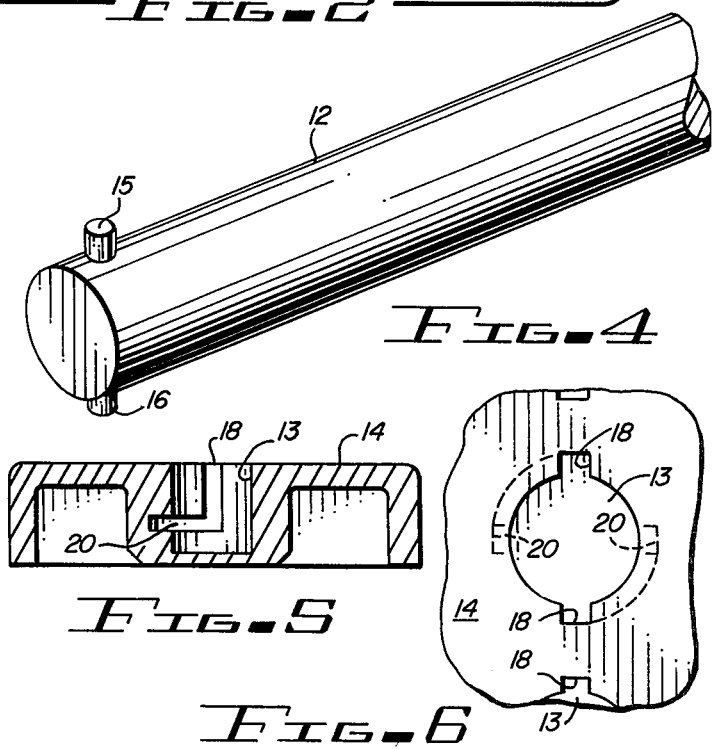
FIG. 5 is a cross-sectional view taken across the width of the embodiment shown in FIG. 2.
Figure 6:
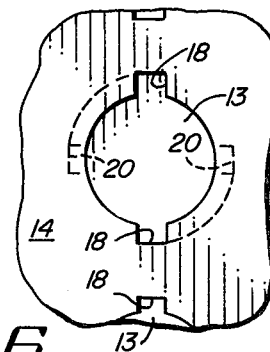
FIG. 6 illustrates details of a portion of the embodiment shown in FIG. 2.

Whenever relocation of the support bar 12 to another one of the apertures 13 is desired, the support bar 12 is rotated clockwise (as shown in FIG. 4) until the projections 15 and 16 rest against the edges of the key-way slots 18. When the support bar 12 is in this position, it then may be withdrawn outwardly from the anchor member 14 and reinserted into another one of the apertures 13 suitable for the next use of the support bar and the X-ray machine with which it is associated.

To insure firm anchoring of the anchor member 14 to the wall adjacent the X-ray machine, a pair of bolts 25 and 26 extend through the anchor member 14 and the wall 30, to which the anchor member 14 is to be attached, through to the other side. On the opposite side of the wall, a plate 31 may be placed, preferrably bridging across at least a pair of the vertical wall supports or 2×4's in the wall. The bolts 25 and 26 then extend through appropriate mating holes in the plate 21, and securing nuts 32 and 33 are tightened to hold the entire assembly together. Other methods of attaching the anchor member 14 to the wall may be used, but the one shown in FIG. 3 is preferred when it is possible to use it because of the firm mounting which is effected by its use.

The anchor member 14 may be made of any suitable material having sufficient strength to accomplish the purpose described. An ideal construction is to make the anchor member as an aluminum casting. The support bar 12 may be a hollow aluminum or stainless steel tube. A clip or holder also may be attached to the anchor member 14 to store the bar 12 flat against the anchor member 14 when the device is not in use.

The foregoing description of the preferred embodiment is to be considered illustrative only and not as limiting of the true scope of the invention, which may be practiced by various equivalents which will occur to those skilled in the art.

I claim:

1. A patient support apparatus including in combination:
   an elongated anchor member for attachment to a wall, said member having a predetermined thickness and having a predetermined number of apertures substantially normal to the surface thereof and extending a predetermined depth therein for receiving a support bar, the walls of said apertures being substantially normal to the surface of said member; and
   an elongated support bar for insertion into said apertures to extend outwardly from said anchor member and having external dimensions to matingly and removably fit into such apertures, said predetermined depth of said apertures being sufficient to cause said support bar to bear against the wall of the aperture into which it is inserted to provide stable support to patients applying weight to said bar in a plane normal to the axis of said support bar.

2. The combination according to claim 1 wherein the apertures in said anchor member extend to a predetermined depth into said anchor member to present an abutment shoulder for establishing the depth to which said support bar may be inserted therein.

3. The combination according to claim 1 wherein the apertures in said anchor member are spaced at predetermined intervals from one another along a straight line.

4. The combination according to claim 3 wherein said anchor member is of an elongated rectangular shape, and the apertures therein are aligned vertically when said anchor member is attached to a wall.

5. The combination according to claim 4 wherein the apertures in said anchor member extend to a predetermined depth into said anchor member to present an abutment shoulder to the end of said support bar inserted therein to establish the maximum depth to which said support bar may be inserted into any of such apertures.

6. The combination according to claim 5 further including bar locking means in each of said apertures; and wherein said support bar includes a mating locking member thereon for engaging said bar locking means in said apertures when said support bar is inserted therein.

7. A patient support apparatus including in combination:

an anchor member of an elongated rectangular shape for attachment to a wall, said member having a predetermined thickness and having a predetermined number of vertically alinged apertures of a predetermined depth therein for receiving a support bar, the depth of said apertures presenting an abutment shoulder for the end of such support bar inserted therein to establish the maximum depth to which such support bar may be inserted into any of said apertures;

a support bar for insertion into said apertures and having external dimensions to matingly and removably fit into said apertures, said predetermined depth thereof being sufficient to cause said support bar to provide stable support to patients applying weight to it in a plane normal to the axis of said support bar;

bar locking means in each of said apertures in the form of a keyway spaced a predetermined distance from the bottom of each of said apertures, each of said apertures further having a keyway access slot formed therein from said keyway to the surface of said anchor member into which said apertures are formed; and a mating locking member on said support bar comprising at least one keyway engaging tab dimensioned to fit into said keyway and located said same predetermined distance from the end of said bar as the distance said keyway is spaced from the bottom of each of said apertures.

8. An accessory for use with medical x-ray apparatus including in combination:

an anchor member for mounting on a wall adjacent said medical x-ray apparatus and having a generally elongated rectangular configuration with a plurality of longitudinally, vertically aligned apertures of a predetermined depth located therein and spaced a predetermined distance from one another for receiving a support bar, the predetermined depth of the apertures presenting an abutment shoulder to be engaged by the end of such support bar inserted therein to establish the maximum depth to which such support bar may be inserted into any of such apertures;

an elongated support bar for insertion into said apertures to extend outwardly therefrom and having external dimensions for snugly and removably fitting into each of said apertures, said support bar bearing against the wall of the aperture into which it is inserted when force is applied to said support bar in a direction perpendicular to the axis thereof; and bar locking means in each of said apertures and a mating locking member on said support bar for engaging said bar locking means in said apertures when said support bar is inserted therein.

9. The combination according to claim 8 wherein said bar locking means comprises a key-way spaced a predetermined distance from the bottom of each of said apertures; each of said apertures has a key-way access slot formed therein from said key-way to the surface of said anchor member into which such apertures are formed, and said locking member on said support bar comprises at least one key-way engaging tab dimensioned to fit into said key-way and located said same predetermined distance from the end of said bar, said engaging tab being free of stress when force is applied to said support bar in a direction perpendicular to the axis thereof.

* * * * *